United States Patent
Wood et al.

(10) Patent No.: US 10,149,882 B2
(45) Date of Patent: Dec. 11, 2018

(54) WEIGHT MANAGEMENT SYSTEMS AND RELATED METHODS

(71) Applicant: NSE Products, Inc., Provo, UT (US)

(72) Inventors: Steven M. Wood, Santaquin, UT (US); Stephen J. Poole, Springville, UT (US); Doug Burke, Orem, UT (US); Mark Bartlett, Orem, UT (US); Angela Mastaloudis, Holladay, UT (US)

(73) Assignee: NSE Products, Inc., Provo, UT (US)

( * ) Notice: Subject to any disclaimer, the term of this patent is extended or adjusted under 35 U.S.C. 154(b) by 53 days.

(21) Appl. No.: 15/483,993

(22) Filed: Apr. 10, 2017

(65) Prior Publication Data

US 2017/0239312 A1    Aug. 24, 2017

Related U.S. Application Data

(63) Continuation of application No. 14/476,675, filed on Sep. 3, 2014, now abandoned.

(60) Provisional application No. 61/873,048, filed on Sep. 3, 2013.

(51) Int. Cl.

| | |
|---|---|
| *A61K 36/00* | (2006.01) |
| *A61K 36/8962* | (2006.01) |
| *A61K 36/33* | (2006.01) |
| *A61K 36/88* | (2006.01) |
| *A61K 36/185* | (2006.01) |
| *A61K 36/752* | (2006.01) |
| *A61K 36/03* | (2006.01) |
| *A61K 36/82* | (2006.01) |
| *A61K 31/352* | (2006.01) |
| *A61K 36/81* | (2006.01) |
| *A61K 36/736* | (2006.01) |
| *A61K 31/198* | (2006.01) |
| *A23L 19/00* | (2016.01) |
| *A23L 33/00* | (2016.01) |
| *A23L 33/105* | (2016.01) |
| *A61K 45/06* | (2006.01) |
| *A61K 9/00* | (2006.01) |
| *A61K 9/14* | (2006.01) |
| *A61K 9/48* | (2006.01) |
| *A61K 31/353* | (2006.01) |
| *A61K 38/00* | (2006.01) |

(52) U.S. Cl.
CPC .......... *A61K 36/8962* (2013.01); *A23L 19/01* (2016.08); *A23L 33/105* (2016.08); *A23L 33/30* (2016.08); *A61K 9/0053* (2013.01); *A61K 9/0095* (2013.01); *A61K 9/14* (2013.01); *A61K 9/48* (2013.01); *A61K 31/198* (2013.01); *A61K 31/352* (2013.01); *A61K 31/353* (2013.01); *A61K 36/03* (2013.01); *A61K 36/185* (2013.01); *A61K 36/33* (2013.01); *A61K 36/736* (2013.01); *A61K 36/752* (2013.01); *A61K 36/81* (2013.01); *A61K 36/82* (2013.01); *A61K 36/88* (2013.01); *A61K 38/00* (2013.01); *A61K 45/06* (2013.01); *A23V 2002/00* (2013.01)

(58) Field of Classification Search
CPC ...................................... A61K 36/00
USPC ........................................ 424/725
See application file for complete search history.

(56) References Cited

U.S. PATENT DOCUMENTS

8,574,656 B2    11/2013    Abelyan et al.

*Primary Examiner* — Michael V Meller
(74) *Attorney, Agent, or Firm* — Thorpe North & Western, LLP; David W. Osborne (57) ABSTRACT

Systems and methods of weight management and compositions or formulations useful therein are disclosed and described.

20 Claims, 1 Drawing Sheet

WEIGHT MANAGEMENT SYSTEMS AND RELATED METHODS

PRIORITY DATA

This is a continuation of U.S. patent application Ser. No. 14/476,675, filed Sep. 3, 2014, which claims the benefit of U.S. Provisional Patent Application Ser. No. 61/873,048, filed Sep. 3, 2013, each of which is incorporated herein by reference.

BACKGROUND

Excessive body weight is becoming a concern around the world, for example, over half of the American adult population is considered to be overweight or obese. Being overweight is associated with several conditions or chronic diseases such as hypertension, elevated cholesterol, type 2 diabetes, stroke, osteoarthritis, and sleep apnea. Economically, the annual costs for excessive body weight on medical expenses and lost income is approximately 70 billion dollars, in the United States alone.

There are many factors that affect body weight or influence a person's ability to lose weight. Many diet programs focus solely on energy (kcals) intake yet the body responds differently to macronutrients (i.e. with simple carbohydrates, the insulin response triggers the body to store fat). Furthermore as dietary energy levels decrease, the body meets its energy demands through utilizing protein and lean body tissue as its primary energy source. Therefore, as a person loses weight there can be a significant loss of muscle which can adversely affect body weight maintenance over the long term. Moreover, if the dieter ceases the diet and gains back some or all of the weight lost, it will typically be as fat. Thus, the dieter may find themselves in an even worse physical condition than when they started the diet as they now weigh the same as before, but have a higher percentage of body fat and lower percentage of muscle.

SUMMARY OF THE INVENTION

A goal for weight management or maintenance should be preservation of lean tissue and utilization of fat stores. With this in mind, dietary protein provides an essential branched chain amino acid, leucine to signal and regulate several processes in the muscle. Interestingly, the majority of dietary protein is consumed primarily at the evening meal which means that throughout the day the body does not have adequate levels of leucine. Furthermore, the typical American consumes mainly carbohydrates for breakfast and lunch signaling the body to store fat.

A number of natural ingredients can assist with the body's ability to burn fat as well as maintain lean body mass (muscle). Furthermore, it is not practical for setting a specific energy dietary level for every body shape and size. As such, important aspects of the present invention include formulations, systems, programs, regimens, and methods which provide weight loss to a subject while minimizing loss of lean muscle tissue. In other words, that majority of weight that is lost is fat. One component of this may be administering formulations that aid the subject with weight loss by for example, stimulating metabolism and energy, reducing hunger signals and food cravings, regulating certain hormones, and providing a sense of wellness, or well-being, including mental and emotional wellbeing. Another component can be administration of sufficient amounts of protein at certain times in order to benefit of the physical aspects of protein consumption (e.g. leucine production, etc.).

In one embodiment, a weight loss system is provided. Such a system can comprise a weight loss accelerator formulation that accelerates weight loss in a subject beginning to utilize the system, a weight loss stimulator formulation that stimulates weight loss in a subject beginning to utilize the system and continues stimulating weight loss with ongoing consumption after completing use of the weight loss accelerator, and a weight loss control formulation that aids a subject in controlling appetite and calorie consumption when said subject is beginning and continuing to utilize the system.

In one embodiment, the weight loss accelerator formulation is administered at least once daily for up to 30 days from the time a user begins using the system. In another embodiment, the weight loss accelerator formulation is administered once daily for a duration of 15 days from the time a user begins using the system.

In one embodiment, the weight loss accelerator is administered as a beverage. In another embodiment, the beverage is prepared from a powder.

In one embodiment, the weight loss accelerator formulation provides a dosage comprising from about 1000 mg to about 3000 mg *opuntia ficus-indicia* (prickly pear) fruit powder; from about 100 mg to about 200 mg *crocus sativus* L. stigma (saffron) fruit powder extract; from about 100 mg to about 200 mg *punica granatum* (pomegranate) fruit extract; and from about 100 to about 200 mg of *citrus sinensis* (blood orange) fruit extract. In another embodiment, the amount of *opuntia ficus-indicia* is about 2000 mg; the amount of *crocus sativus* L. stigma is about 177 mg; the amount of *punica granatum* is about 150 mg; and the amount of *citrus sinensis* is about 125 mg.

In one embodiment, the weight loss stimulator formulation is administered at least once daily for up to 360 days from the time a user begins using the system. In another embodiment, the weight loss stimulator formulation is administered daily for up to 90 days from the time a user begins using the system. In a further embodiment, the weight loss stimulator formulation is administered to the subject within 30 minutes of eating each meal. In yet a further embodiment, the weight loss stimulator formulation is in an oral dosage capsule form.

In one embodiment, the weight loss stimulator formulation provides a dosage comprising a *citrus sinensis* (red orange) fruit extract in amount of from about 50 mg to about 250 mg; a *undaria pinnatifida* (brown seaweed) extract in an amount of from about 50 to about 250 mg; a *camellia sinensis* (green tea) leaf extract in an amount of about 30 to about 150 mg; *citrus* bioflavonoids in an amount of from about 20 mg to about 100 mg; quercetin (an *allium cepa alliaceae* (onion) bulb extract) in an amount of from about 10 mg to about 75 mg; and a *capsicum annum* L. (cayenne) fruit powder in an amount of from about 10 mg to about 52 mg. In another embodiment, the amount of *citrus sinensis* fruit extract is about 83.3 mg; the amount of *undaria pinnatifida* extract is about 83.3 mg; the amount of *camellia sinensis* leaf extract is about 50 mg; the amount of *citrus* bioflavonoids is about 33.3 mg; the amount of quercetin is about 25 mg; and the amount of *capsicum annum* L. fruit powder is about 16.7 mg in an individual unit dosage.

In one embodiment, three individual unit dosage forms of weight loss control formulation are administered daily. In another embodiment, the weight loss control formulation is administered at least once daily for up to 360 days from the time a user begins using the system. In another embodiment, the weight loss control formulation is administered daily for up to 90 days from the time a user begins using the system.

In one embodiment, the weight loss control formulation provides a dosage comprising a *theobroma cacao* (cocoa) bean powder extract in an amount of from about 150 mg to about 1500 mg; a *prunus cersus* (tart cherry) fruit powder extract in an amount of from about 75 mg to about 600 mg; a *punica granatum* (pomegranate) fruit extract in an amount of from about 60 mg to about 500 mg; and a *camellia sinensis* (green tea) leaf extract with added L-theanine in an amount of from about 100 mg to about 860 mg. In another embodiment, the amount of *theobroma cacao* extract is about 187.5 mg; the amount of *prunus cersus* extract is about 75 mg; the amount of *punica granatum* extract is about 62.5 mg; and the amount of *camellia sinensis* extract is about 107.5 mg in an individual dosage unit.

In one embodiment, four individual unit dosage forms of weight loss control formulation are administered daily. In another embodiment, two individual unit dosage forms are administered prior to two meals. In yet a further embodiment, administration is within 30 minutes prior to the meals.

In one embodiment, the weight management system, program, regimen, or method can include a protein supplement that can be consumed by the subject as needed to maintain a minimum daily protein intake. In another embodiment, the protein supplement provides at least 30 grams of protein.

In an additional embodiment, a weight loss system according to the present invention can comprise:

a weight loss accelerator formulation that accelerates weight loss in a subject beginning to utilize the system, said accelerator formulation providing a dosage comprising about 2000 mg *opuntia ficus-indicia* (prickly pear) fruit powder, about 177 mg *crocus sativus* L. stigma (saffron) fruit powder extract, about 150 mg *punica granatum* (pomegranate) fruit extract, and about 125 mg of *citrus sinensis* (blood orange) fruit extract;

a weight loss stimulator formulation that stimulates weight loss in a subject beginning to utilize the system and continues stimulating weight loss with ongoing consumption after completing use of the weight loss accelerator, said stimulator formulation providing a dosage comprising about 83.3 mg of a *citrus sinensis* (red orange) fruit extract, about 83.3 mg of a *undaria pinnatifida* (brown seaweed) extract, about 50 mg of a *camellia sinensis* (green tea) leaf extract, about 33.3 mg of *citrus* bioflavonoids, about 25 mg of quercetin (an *allium cepa* alliaceae (onion) bulb extract), and about 16.7 mg *capsicum annum* L. (cayenne) fruit powder; and a weight loss control formulation that aids a subject in controlling appetite and calorie consumption when said subject is beginning and continuing to utilize the system, said weight loss control formulation provides a dosage comprising about 187.5 mg *theobroma cacao* (cocoa) bean powder extract, about 75 mg of a *prunus cersus* (tart cherry) fruit powder extract, about 62.5 mg of a *punica granatum* (pomegranate) fruit extract, and about 107.5 mg of a *camellia sinensis* (green tea) leaf extract with added L-theanine wherein one unit dosage of the weight loss accelerator formulation is administered once daily for a duration of about 15 days from the time that a user commences the program and three unit dosages of the weight loss stimulator are individually administered once daily for a duration of about 90 days from the time that a user commences the program, and two unit dosages of the weight loss control formulation are administered twice daily.

The weight management methods, systems, programs and regimens of the present invention additional encompass a weight loss regimen comprising administering a weight loss accelerator formulation to a subject at the beginning of the regimen, administering a weight loss stimulator formulation to the subject at the beginning of the regimen concurrently with the weight loss accelerator formulation and continuing after cessation of the weight loss accelerator formulation, and administering a weight loss control formulation to the subject concurrently with the weight loss stimulator formulation.

In one embodiment, a protein supplement can be administered to the subject concurrently with all previously recited weight loss formulations in order to maintain a minimum daily protein intake.

In another embodiment, the weight loss accelerator is administered to the subject for a period of 15 days at the beginning of the regimen. In a further embodiment, the weight loss stimulator and control formulations are administered to the subject for a period of 90 days.

In yet another embodiment, the regimen includes a dietary or eating plan as further recited herein. In one embodiment, such an eating plan delivers 6 portions of protein, 2 portions of vegetables, 2 portions of fruit, and 2 portions of complex carbohydrates per day. In an additional embodiment, each portion has a size based on the subjects hand size and approximately one handful equals approximately one portion.

In addition to the foregoing, the present invention encompasses methods of managing, regulating, or controlling weight in a subject. Furthermore, in some embodiments, weight loss occurring employing such methods can minimize the loss of lean muscle tissue and maximize the loss of fat. In some embodiments, substantially no muscle tissue is lost. Such a method can include any and all activities described or otherwise inferred herein, including engaging the subject in a weight loss regimen as discussed and/or administering the disclosed and described weight loss systems to the subject.

EXAMPLE EMBODIMENTS

Before the present invention embodiments are disclosed and described, it is to be understood that the invention embodiments are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

In describing and claiming the present invention, the following terminology will be used.

The singular forms "a," "an," and "the" include plural referents unless the context clearly dictates otherwise. Thus, for example, reference to "a carrier" includes reference to one or more of such carriers, and reference to "an excipient" includes reference to one or more of such excipients.

As used herein, "formulation" and "composition" may be used interchangeably, and refer to a combination of two or more elements, or substances. In some embodiments a composition may include an active agent in combination with a carrier or other excipients, adjuvants, etc.

As used herein, "effective amount" refers to an amount of an ingredient which, when included in a composition, is sufficient to achieve an intended compositional or physiological effect. Thus, a "therapeutically effective amount" refers to a non-toxic, but sufficient amount of an active agent, to achieve therapeutic results in treating or preventing a condition for which the active agent is known to be effective. Likewise, an "effective amount" of a formulation or composition is an amount sufficient to achieve a desired or intended physiologic effect. It is understood that various biological factors may affect the ability of a substance or formulation to perform its intended task. Therefore, an "effective amount" or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine.

As used herein, "subject" refers to a mammal that may benefit from the administration of a system, composition, program, routine, regimen, formulation, or method as recited herein. In one aspect, the subject can be a mammal. In one aspect, the subject can be human.

As used herein, "administration," and "administering" refer to the manner in which an agent, or composition containing such, is presented to a subject. Administration can be accomplished by various routes well-known in the art such as oral and non-oral methods.

As used herein, "oral administration" refers to a route of administration that can be achieved by swallowing, chewing, or sucking of an oral dosage form comprising the drug. Examples of well-known oral dosage forms include tablets, capsules, caplets, powders, granulates, beverages, syrups, elixirs, confections, or other food items, etc.

As used herein, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a concentration range of 0.5 to 400 should be interpreted to include not only the explicitly recited concentration limits of 0.5 and 400, but also to include individual concentrations within that range, such as 0.5, 0.7, 1.0, 5.2, 8.4, 11.6, 14.2, 100, 200, 300, and sub-ranges such as 0.5-2.5, 4.8-7.2, 6-14.9, 55, 85, 100-200, 117, 175, 200-300, 225, 250, and 300-400, etc. This interpretation should apply regardless of the breadth of the range or the characteristic being described.

As used herein, the term "about" means that dimensions, formulations, parameters, and other quantities and characteristics are not and need not be exact, but may be approximated and/or larger or smaller, as desired, reflecting tolerances, conversion factors, rounding off, measurement error and the like and other factors known to those of skill. Further, unless otherwise stated, the term "about" shall for the sake of convenience also provide express support for the term "exactly," regarding ranges and numerical data. In other words, support shall be provided for the exact numerical value or range with which the term "about" is associated.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

A goal for weight management or maintenance should be preservation of lean tissue and utilization of fat stores. Dietary protein provides an essential branched chain amino acid, leucine, to signal and regulate several processes in the muscle. For most humans, the majority of dietary protein is consumed primarily at the evening meal which means that throughout the day the body does not have adequate levels of leucine. Furthermore, the typical American consumes mainly carbohydrates for breakfast and lunch signaling the body to store fat.

In some invention embodiments, a weight management or maintenance system, program, or method can include a nutritional supplement component, a dietary component, an exercise component, or any combination thereof. In some embodiments, the combination of two or more components can provide unexpected and surprising benefits as compared to use of a single component. In some aspects, the two components can be the nutritional supplement component and the dietary component.

Regarding the nutritional supplement component, in some embodiments, such component can include one or more nutritional or dietary supplements administered to a subject that positively impact bodily function, cognition, emotion, and/or metabolism. In some aspects, the dietary supplements can assist the body to utilize fat to meet energy demands, maintain muscle, and improve sense of wellbeing and motivation. Specific ingredients selected for inclusion in such dietary supplements either have been, or can be, identified by gene expression studies. One example of such selection process can be rodent studies, examining supplement impact to the subject's gene expression profile in muscle, adipose, and brain tissues. As such, in some aspects administration of such supplements can regulate expression of certain genes in a subject taking the supplements that are involved in weight management issues, such as fat storage, muscle building, metabolic rate, energy, etc.

On such supplement is referred to herein as a "weight loss accelerator formulation". Such a supplement can be prepared in order to be used at commencement of a weight loss, or management program in accordance with certain invention embodiments. Such a supplement or formulation can provide initial benefits that accelerate initial weight loss with increased retention of lean muscle tissue. Effects, such as appetite suppression, metabolic rate increase, and selection of fat burning as compared to lean muscle tissue consumption for energy are sought with the goal of aiding an initial burst of weight loss activity. It has been found that a subject who experiences dramatic initial weight loss results when beginning a weight management program will gain enthusiasm and a mental and emotional boost that provides excitement and enthusiasm which helps them proceed into longer term phases of such a program with a greater percentage of success.

A number of specific ingredients can be included in such a weight loss accelerator supplement, and such ingredients can be selected and combined based at least in part on the gene expression results achieved during testing. Examples of ingredients that can be combined into various formulations are shown in Table 1. In some embodiments, the amount of active agent present in each of formulations 1-8 can be representative of a single unit dosage form, such as one capsule, beverage, etc. as recited further below.

TABLE 1

Active Agents of Exemplary Accelerator Formulation Dosages

| Ingredient | 1 | 2 | 3 | 4 | 5 | 6 | 7 | 8 |
|---|---|---|---|---|---|---|---|---|
| Garcinia Cambogia | | | | 1333 | | | | |
| Glucomannan | | | | | | | 2000 | |
| Maltodextrin | | | | | | 9500 | | |
| Opuntia ficus-indica fruit powder (Cactinea) | 2000 | 2000 | 2000 | 2000 | 2000 | 2000 | | 2000 |
| Opuntia Milpa Alta | | | | | | | | |
| Pomegranate extract | 150 | 150 | 150 | 150 | | | | |
| Pomegranate extract RU | | | | | 150 | | | |
| Pomegranate juice conc pwd | | | | | | 300 | 300 | 300 |
| Soy Protein Isolate | | | | | | | | 300 |
| Red Orange Complex H | 125 | 125 | 125 | 125 | | 125 | | |
| Red Orange Complex H Water | | | | | 125 | | | |
| Red Orange juice pwd | | | | | | | 375 | 375 |
| Satiereal | 177 | 177 | 177 | 177 | 177 | 177 | | |

Amounts Per Day in mg for Label and Formula

An additional type of supplement that can be used as part of the systems, programs, regimens, or methods recited herein is referred to as a "weight loss stimulator" formulation. Such a supplement can help maintain or elevate metabolic rate, energy, and stamina as well as reduce hormones and other endogenous substances produced by the body in response to stress, such as cortisol and inflammation among other effects. Such formulation can aid the body's metabolism to utilize fat while maintaining muscle mass. A number of specific ingredients can be included in such a weight loss stimulator supplement, and such ingredients can be selected and combined based at least in part on the gene expression results achieved during testing. Examples of ingredients that can be combined into various formulations are shown in Table 2. In some embodiments, the amount of active agent present in each of formulations 9-16 can be representative of a single unit dosage form, such as one capsule, beverage, etc. as recited further below.

TABLE 2

Active Agents of Exemplary Stimulator Formulation Dosages

| Ingredient | 9 | 10 | 11 | 12 | 13 | 14 | 15 | 16 |
|---|---|---|---|---|---|---|---|---|
| Cayenne Powder | 50 (50) | 50 (50) | 50 (50) | 50 (50) | 50 (50) | 50 (50) | 50 (50) | |
| Chromium Yeast | | | | | | | | 0.12 (60) |
| Citrus Bioflavonoids | 100 (210) | 100 (210) | 100 (210) | 100 (210) | 100 (210) | | 100 (210) | |
| Citrus Bioflavonoids EU | | | | | | 100 (210) | | |
| Coleus Forskohlii extract 10% | | | | | | | 500 (515) | |
| Fucoxanthin (Seaweed extract) | 2.5 (263) | 2.5 (263) | | | | | 2.5 (263) | |
| Glucomannan | | | | | | | | 2600 (2600) |

TABLE 2-continued

Active Agents of Exemplary Stimulator Formulation Dosages

| Ingredient | 9 | 10 | 11 | 12 | 13 | 14 | 15 | 16 |
|---|---|---|---|---|---|---|---|---|
| Green Tea Extract 35% Theanine | | | | | | | | 150 (429) |
| Green Tea Extract 50% | | | | | | 300 (316) | | |
| Green Tea Extract 97% | 150 (158) | 150 (158) | 150 (158) | 150 (158) | 150 (158) | | 150 (158) | 500 (500) |
| Lotus Leaf | | | | | | | | 300 (300) |
| Magnolia Bark Extract | | | | | | | | 300 (300) |
| Powergrape | | | | 400 (412) | 400 (412) | 400 (412) | 400 (412) | |
| Quercetin - Onion Extract | 250 (263) | | 250 (263) | 250 (263) | 250 (263) | 250 (263) | | |
| Quercetin - Saphora Japonica | | 75 (93.7) | | | | | 75 (93.7) | |
| Red Orange Complex ROCH | 250 (263) | 250 (263) | 250 (263) | 250 (263) | 250 (263) | | 250 (263) | |
| Red Orange Complex ROCH EU | | | | | | 250 (263) | | |

Amounts Per Day in mg for Label (Amounts Per Day in mg for Formula)

A further formulation or supplement that can be used as part of the systems, programs, regimens, or methods recited herein is referred to as a "weight loss control" formulation or supplement. Such a supplement can continue to moderate appetite control, provide amino acids for muscle mass maintenance, and maintain metabolism levels, among other effects. A number of specific ingredients can be included in such a weight loss control supplement, and such ingredients can be selected and combined based at least in part on the gene expression results achieved during testing. Examples of ingredients that can be combined into various formulations are shown in Table 3. In some embodiments, the amount of active agent present in each of formulations 17-24 can be representative of a single unit dosage form, such as one capsule, beverage, etc. as recited further below.

Finally, the stimulator can be removed while the control formulation is continued. In another embodiment, the accelerator formulation can be administered first for a specified period, and then stopped and the stimulator formulation can be administered for a specified period of time and then stopped, and finally, the control formulation can be administered for a specified period of time. In a further embodiment, the accelerator formulation can be administered for a specified period of time and then the stimulator and control formulations can be added, either consecutively or simultaneously.

In one aspect, the accelerator, stimulator and control formulations can be administered for a specific period of time. In some aspects, the period or amount of time may be the same. In other aspects, the periods may be different. In

TABLE 3

Active Agents of Exemplary Control Formulation Dosages

| Ingredient | 17 | 18 | 19 | 20 | 21 | 22 | 23 | 24 |
|---|---|---|---|---|---|---|---|---|
| Banaba Extract | | | | | 48 (49.4) | | | |
| Chromium Chelate | | | | | | | | |
| Cocoa Powder | 750 (788) | 750 (788) | 750 (788) | 750 (788) | 750 (788) | 750 (788) | 750 (774) | 750 (788) |
| Green Tea Extract 35% Theanine | 150 (450) | 150 (450) | 150 (450) | 160 (450) | | | | |
| L-Carnitine (as tartrate) | | | | | | | | |
| Maltodextrin | | | | 1228 (1228) | | | | |
| Pomegranate extract | 250 (258) | 250 (258) | 250 (258) | 250 (258) | 250 (258) | 250 (258) | | |
| Pomegranate extract EU | | | | | | | 250 (258) | |
| Pomegranate juice powder | | | | | | | | 250 (258) |
| Red Orange Juice Powder | | | | | | | | 250 (258) |
| Tart Cherry powder | 300 (309) | 300 (309) | 300 (309) | 300 (309) | 300 (309) | 300 (309) | 300 (309) | 300 (309) |
| Theanine 98% | | | | | 150 (161) | 150 (161) | | |

Amounts Per Day in mg for Label (Amounts Per Day in mg or Formula)

The foregoing formulations can be utilized in any manner that supports or achieves a specifically desired weight management or maintenance program, method or regimen. In one embodiment, the formulations can be administered simultaneously for a predetermined or specified duration or amount of time. In another aspect, the formulations can be administered separately at specifically desired or determined times as needed in order to provide or assist in the weight maintenance program. Furthermore, in yet a further aspect, all of the formulations can be initially administered and then one formulation removed from administration while the other two are maintained, and then a second formulation can be removed while one is maintained. In one embodiment, the accelerator, stimulator, and control formulations can be administered simultaneously for a given time, duration, or period. Next, the accelerator formulation can be removed and the stimulator and control formulations continued.

one aspect, the amount of time may be from about 1 week to about 1 year. In another aspect, the amount of time may be from about 2 weeks to about 2 years. In an additional aspect, the amount may be about 15 days. In another aspect, the amount may be for about 90 days. In one embodiment, a weight management or weight loss system, program, or method, can include administration of a weight loss accelerator formulation for 15 days and administration of a weight loss stimulator and a weight loss control formulation for 90 days. In such embodiment, all three formulations or supplements are taken for the first 15 days of the program or method and then the weight loss accelerator is discontinued and the weight loss stimulator and control formulations are taken for the remainder of the 90 day period.

In addition to variations in timing and duration, the dosage or amount of each supplement can be varied. Further the dosage type can be varied. In one aspect, the formulations can be oral formulations selected from tablets or capsules, or can be a foodstuff, such as a beverage (including a powder to be added to liquid and consumed as a beverage), shake, bar, pastry, a confection, etc. In one aspect, the supplements or formulations can be a beverage. In another aspect, the supplements or formulations can be capsules. In yet a further aspect, the weight loss accelerator formulation can be a beverage and the weight loss stimulator and control formulations can be a capsules.

Regarding dosage amounts in one aspect, the formulations recited herein can be administered to a subject from 1 to 4 times per day. In one aspect, the number of daily administrations may be 1. In another aspect, the number of daily administrations may be 2. In yet a further aspect, the number of daily administrations may be 3. In still a further aspect, the number of daily administrations may be 4. In one specific embodiment, a weight loss accelerator formulation as recited herein can be administered once per day. In another embodiment, the weight loss stimulator and control formulations can be administered two times per day. In one aspect, administrations can be with meals. In another aspect, administration can be just prior to meals, for example 15 to 20 minutes prior to a meal. In one aspect, the number of unit dosage forms received at each administration can vary depending on the amount of active ingredient in each. In some embodiments, a single unit dosage (i.e. one beverage or one capsule) may be sufficient to provide the total amount of active agent desired at the administration time. In another embodiment, multiples of each single unit dosage form (i.e. two, three, four, capsules) can be administered in order to provide the total amount of active agent desired at the administration time. In one specific embodiment, one unit dosage of a weight loss activator formulation can be administered, for example, one beverage. In one embodiment, such unit dosage can have one or all of the active ingredients in the amounts of the exemplary unit dosages recited in Table 1. In some aspects, the amount of the active agents may be a fraction, or a multiple of thereof, such as one quarter, one half, double, triple, quadruple, etc. Nearly any amount or fraction of active ingredient can be used in specific unit dosages, which is sufficient to be deemed an effective amount. This same principle is true for the weight loss stimulator and control formulations recited in Tables 2 and 3 respectively.

In one embodiment, a weight loss activator formulation may be provided as a powder having the active agents recited in the formulations of Table 1, in the amounts specified as a single unit dosage. In some embodiments, such a dosage can be administered one time per day for 15 days at the commencement of a weight management program or method. In an additional embodiment, a weight loss stimulator formulation may be provided as a capsule having the active agents recited in the formulations of Table 2, in the amounts specified as a single unit dosage. In some embodiments, such a dosage can be administered 1-3 times per day. In one embodiment, such a dosage can be administered 3 times per day and in some embodiments can be administered just prior to each meal, such as 15-20 minutes prior. In other embodiments, the amounts shown in Table 2 can represent a total daily dosage and single unit dosages can be administered as a fraction thereof, for example, 3 capsules administered daily in order to provide the total amount of active agent listed. In yet a further embodiment, a weight loss control formulation can be provided as a capsule having the active agents recited in the formulations of Table 3, in the amounts specified as a single unit dosage. In some embodiments, such a dosage can be administered 1-4 times per day.

In one embodiment, such a dosage can be administered 4 times per day. In one embodiment, unit dosages (i.e. two capsules) can be administered twice per day. In a further embodiment, such administration can occur just prior to a meal, such as 15 to 20 minutes prior. In other embodiments, the amounts shown in Table 3 can represent a total daily dosage and single unit dosages can be administered as a fraction thereof, for example, 2 capsules twice daily for a total of 4 capsules per diem.

In addition to the active agents (a further description of which is provided below), a number of other ingredients can be included in order to provide specific dosage forms. For example, carriers, thickeners, diluents, etc. such as gelatin, starch, cellulose (including microcrystalline cellulose), silicon dioxide, water, etc. can be used. However, in other dosage forms, only the active agents may be present without the substantial addition of other ingredients.

In one embodiment, a weight loss accelerator formulation is designed to assist a subject begin to lose weight and see initial success immediate, observable changes in achieving a healthy body weight (within the first 15 days). The weight loss accelerator formulation can in one embodiment, be a powder that is designed to easily be mixed into an amount of water, for example, approximately 240 mL of water or other beverages and to be consumed once a day.

In one embodiment, the ingredients of the weight loss accelerator formulation can include Prickley Pear Cactus fruit powder (i.e. *opuntia ficus*-indica extract), red orange complex (i.e. *citrus sinensis* fruit extract), Satiereal® Saffron (i.e. *crocus sativa* extract), and pomegranate juice powder concentrate (i.e. *punica granatam* fruit extract), and maltodextrins.

Red orange extract can inhibit damage caused by oxidative stress and inhibit the accumulation of body fat. The accumulation of unwanted body fat is influenced by a number of factors including inflammation, oxidative stress and abnormal insulin signaling. Fat accumulation can be inhibited by antioxidants, including those found in blood oranges. For example consumption of blood orange juice lead to a reduction in body weight, inhibited fat accumulation and attenuated diabetes prevalence in an obese rat model. Furthermore, gene expression analysis of the adipose tissues demonstrated that the blood orange juice feeding opposed a majority of the gene expression changes elicited by the high fat diet. This data supports a causal role between gene expression changes and inhibition of fat accumulation by blood orange. The positive effects elicited by the blood orange juice were not observed with typical orange juice (Navelina), indicating that factors unique to the blood orange variety confer its anti-obesogenic benefits.

*Crocus sativus* is a commonly used spice (saffron) in India, Persia, Greece, and Italy. It is derived from stigmas harvested from *Crocus sativa* L, the saffron *crocus*. This spice is commonly grown in the eastern zone of the Mediterranean basin. Saffron has been an important flavoring in risotto, bouillabaisse, and paella, and in Indian and Persian aromatic rice dishes, sauces, and desserts. Historical uses of saffron include easing digestion of spicy food, soothing of irritated stomachs, and in the Middle East to treat depression and melancholia. In 200 mg of a *crocus sativus* extract there is 33 mg of saffron, equivalent to that found in about ½ serving of paella. *Crocus sativus* extract is also a source of 3 natural compounds found in saffron, i.e. Crocin (color), picrocin (bitterness), and safranal (odor and aroma). *Crocus sativa* has been consumed safely for centuries, and the extract of Saffron is listed in US FDA GRAS lists (21 CFR 182.20).

*Crocus sativus* extract can effect satiety by decreasing stress and improving emotional health. One substance in the body that influences food intake is serotonin. Serotonin is a neurotransmitter that influences anxiety, mood, appetite, satiety, and compulsiveness. *Crocus sativus* has positive influences serotonin levels and leads to improved emotional behavior, exertion of a satiating effect, and decreased compulsive snacking.

An edible fruit native to Persia, pomegranate is grown and consumed throughout the world, including the United States, and has been revered through the ages for its medicinal properties. Pomegranate juice or its extracts have positive effects on fat reduction; many of these effects have been attributed to their very high levels of antioxidants, including polyphenols, flavonoids, anthocyanins, and tannins. Pomegranate extract provides flavor and color to this product but also adds benefits to help suppress appetite and influence gene expression.

Maltodextrins (oligosaccharides) are complex carbohydrates and can be included in the present formulations to provide some energy source but prevents the insulin spike from simple carbohydrates. They provide a more sustained release of carbohydrates vs simple carbohydrates. Oligosaccharides have been shown to influence hormones that control appetite.

Glucomannan is a water-soluble fiber that is derived from the root of the konjac plant (*Amorphophallus konjac*). *Amorphophallus konjac* was originally cultivated in China over 2,000 years ago, and spread to Japan around 500 A.D. Historically the tuber has been processed and prepared as flour for noodles and a jelly called "konjaku".

Water soluble glucomannan has been shown to slow glucose release from the digestive tract in amounts proportional to their viscosity. Thus, glucomannan's glucose stabilizing benefits are likely to be in large part due to its high viscosity. When a carbohydrate meal is consumed with glucomannan, it forms a dense gel-matrix leading to a more gradual release of sugar into the blood stream, which in turn reduces the insulin spike that is typical after a meal. Glucomannan leads to a reduction in blood sugar variation, and the meal is more like a low-glycemic index (GI) meal rather than a high-GI entity. All this may help increase satiety from a meal.

Generally, the weight loss stimulator formulations of the present invention are designed to provide nutritional support for weight management by increasing metabolism and achieving a visible change in silhouette. Lean body tissue (skeletal muscle) is the most metabolically active tissue in the body, even while the body is at rest. The greater amount of lean body mass that an individual has, the greater their Resting Metabolic Rate (RMR), which is the amount of kcals that they burn while at rest. During any weight loss program, individuals lose both body fat (a desired effect) and lean body mass (muscle) (an undesired effect) as they lose total kilograms of body weight. Consequently, even if individuals achieve their goal body weight, they typically have lower lean body mass at the end of the diet and a corresponding lower RMR. The result is that it is more difficult to maintain weight loss because of the depletion of lean body mass and lower metabolic rate at rest. Therefore, one key to achieving and more importantly, maintaining a healthy body weight, is to retain as much lean body mass as possible during any weight loss program. An intervention that increases the mobilization and utilization/oxidation of fat as a fuel source during weight loss would in turn spare lean body mass as the body would be burning fat rather than protein (muscle) to fuel activity. Weight loss stimulator formulations as recited herein are specifically formulated to support increased fat metabolism and preservation of lean body mass during weight loss. The ingredients can in some embodiments include without limitation: Red Orange Complex, Green Tea Extract, Fucoxanthin, Whole Grape Extract, Onion Extract (standardized for quercetin), *Citrus* Bioflavonoids and Cayenne Powder.

As previously mentioned, red (Moro) oranges (also known as blood oranges) are a unique variety of *citrus* fruit in that they contain an unusual group of antioxidant pigments known as anthocyanins that give the *citrus* fruit a dark red, almost purple, color. Red oranges have been studied for their unique effects both in juice and in extract forms. Weight loss stimulator formulations as recited herein can include a red orange extract that has been shown to inhibit damage caused by oxidative stress and to inhibit the accumulation of body fat.

Significant thermogenic (energy expenditure at rest), fat burning and weight loss can be achieved by administration of green tea extract. For example, supplementation with caffeinated green tea (375 mg catechins/day) can increase total energy expenditure, including increased fat oxidation in subjects. Caffeine alone has no effect on thermogenesis or fat oxidation (fat burning) suggesting that it is the green tea catechins, not the caffeine responsible for the positive thermogenic and fat burning effects. Similarly, consumption of green tea can lead to reductions in overall body weight, waist circumference and total fat mass, further supporting the role of green tea in promoting weight loss, specifically fat loss. Of note, waist/hip circumferences and visceral, or 'belly fat' can all be preferentially reduced. In addition to directly reducing body fat stores, the preferential use of fat as a fuel reduces spares protein from oxidation for fuel, thus protecting muscle protein. This muscle sparing effect by green tea can occur where green tea supplementation elicits a sparing of lean muscle mass.

Brown seaweed extract (containing a xanthophyll-carotenoid, Fucoxanthin) can increase fat metabolism, particularly in animals on a high fat diet. For example, mice fed a high fat diet and supplemented with fucoxanthin for 10 weeks experienced a significant decrease in body weight and adipose tissue. Brown seaweed extract containing fucoxanthin increases fat oxidation (burn) as well as heat production in the mitochondria of adipose tissue. Subjects further benefit from reductions in liver and body fat. In some instances, brown seaweed extract can improve body shape even in the absence of weight loss. During a study, present inventors observed that brown seaweed extract and pomegranate seed oil for 12 weeks led to reductions in thigh circumference and other key body measurements in the absence of weight loss. As this was not a weight loss study, but instead designed to investigate the effects of the supplement on body shape, these findings support the premise that brown seaweed extract can improve body shape/silhouette, even in the absence of weight loss.

Diet and exercise are typically components of an effective weight management program. Whole grape extract has been included in embodiments of weight loss stimulator formulations facilitate exercise performance and post-exercise recovery. Whole grape extract supplemented at 400 mg/day in handball players, significantly enhanced overall physical performance (19.5 vs. 4.4%) and protected against muscle damage compared to a control group. The enhancement of physical performance directly correlated with a decrease in plasma markers of muscle damage (creatine kinase (CPK)). By protecting against exercise-induced muscle damage and enhancing recovery following exercise, whole grape extract supports the exercise component of the program. Exercise contributes to fat metabolism and building and retention of lean muscle mass.

Quercetin (i.e. onion extract) can attenuate both insulin resistance (the inability to use insulin effectively for glucose metabolism) and inflammation associated with obesity. In human adipocyte (fat cell) cultures, quercetin inhibits the expression of pro-inflammatory genes. In obese rats, quercetin at 10 mg/kg-body weight reduced body weight gain. Remarkably, in 3T3-L1 pre-adipocytes, quercetin induced apoptosis (cell suicide) in a dose- and time-dependent manner, and had the most powerful effects on these cells of the 6 flavonoids tested suggesting that quercetin may have the ability to reduce the total number of fat cells in the body. Quercetin supplementation reduces abdominal fat, lower systolic blood pressure and attenuates abnormal structure and function changes in heart and the liver in rats on a high-fat, pro-inflammatory diet. Quercetin supplementation also opposed negative changes in gene expression elicited by the high fat diet. Studies in mice have confirmed these positive effects of quercetin on gene expression related to its anti-obesogenic, anti-oxidative effects and anti-inflammatory benefits. Analogous to the effects of whole grape extract, quercetin improves exercise tolerance in mice and enhances physical performance in humans, indicating that it too, is a supportive ingredient for the promotion of exercise in a weight management program.

*Citrus* fruit is an exceptionally good source of bioflavonoid antioxidants. Flavonoids may help to promote the achievement and maintenance of a healthy body weight, as they confer a number of benefits associated with weight management: antioxidant function, cellular protection, and blood glucose control. For example, overweight cats fed a saturated fat diet fortified with *citrus* bioflavonoids, responded with lower energy intakes, lower plasma lipids and lower concentrations of oxidative damage markers, suggesting that *citrus* bioflavonoids may support weight management. In some embodiments, the *citrus* bioflavonoid complex ingredient in weight loss stimulator formulations is derived from a blend of 100% natural *citrus* extracts, including oranges, limes, lemons, tangerines, and grapefruit, and is classified as Generally Regarded as Safe.

Capsaicin, an active component of hot peppers, is commonly used as food stuff around the world and is typically consumed in the form of cayenne powder. Several epidemiological studies have identified that populations that consistently consume capsaicin have lower incidences of obesity. Capsaicin has been shown to increase thermogenesis through enhanced adrenal gland secretion of catecholamines, a class of substances known to increase metabolic rate. For example, in a comparison rats fed either capsaicin or saline (control group) there was a decrease in body weight of 8% in mice fed capsaicin, a result attributed to increases metabolism in the capsaicin treated group.

Chromium (Cr) supplementation promotes healthy blood glucose metabolism without any documented side effects. Clinical studies show that Cr supplementation improves glucose tolerance, and decreases hemoglobin glycosylation in people with type 2 diabetes.

An important component of achieving and maintaining healthy body weight is appetite control. Furthermore, as someone begins a weight loss program it is important to have willpower as well reduction of stress to help achieve the desired goals. Weight loss control formulations as recited herein assist in the control of appetite and to provide nutritional support while restricting energy. Further, such formulations comprise ingredients that promote relaxation, such as theanine, facilitate recovery from exercise such as tart cherry powder, and regulate blood sugar and inflammation, which in turn may help control appetite. The net effect can be aid in controlling appetite and anxiety, and recovery from exercise, thereby facilitating adherence. Additionally reduction of fat can be increased. This formulation contributes to willpower and assists in healthy weight management. The ingredients in some embodiments may include without limitation: cocoa powder, green tea extract (35% theanine), tart cherry powder, chromium chelate, pomegranate extract or juice powder.

In many cultures around the world, chocolate and cocoa are very popular foods, where cocoa has both food/flavor and medicinal benefits. Chocolate is a rich source of flavanols (including epicatechin/catechin), more than beans, cherries, tea, and wine. Cocoa consumption can aid in control weight and appetite. It has been found that mice fed cocoa powder along with high fat or normal fat diets experience reduced weight gain, attenuated insulin resistance, and reduced high fat induced liver disease. These benefits seem to be via cocoa powder's influence on effects of pro-inflammatory pathways in white adipose tissues.

In addition to the above-recited benefits, green tea or green tea extract is thought to decrease anxiety and increase relaxation. Green tea extract containing theanine may improve relaxation. For example, subjects fed theanine at 50-200 mg/day experience a sense of relaxation in approximately 30-40 minutes.

Tart cherries contain polyphenols that have particularly good antioxidant effects. Interestingly tart cherries also have anti-inflammatory and positive effects on body weight. Tart cherry also decreases the gene expression of inflammatory markers.

Exercise can be an important part of weight management and tart cherries positively influence recovery from exercise and inflammation following exercise. Acute muscle damage is caused by long distance running, resulting in inflammation and decreased force production. The ingestion of tart cherry juice (TCJ), improve delayed onset of muscle soreness (DOMS).

As previously mentioned, Pomegranate juice or its extracts have positive effects on fat reduction, many of which are attributed to their very high levels of antioxidants, including polyphenols, flavonoids, anthocyanins, and tannins. Various mechanisms have been proposed on how different extracts of pomegranate help in fat reduction, one of which is the effects of pomegranate fruit extract on resistin.

Pomegranate extract can in some embodiments, be included as a component of the weight loss control formulations and supplements recited herein, providing a number of supportive benefits for weight management. Firstly, overweight and obesity are associated with increased levels of stress, both psychological and oxidative, as well as inflammation. Higher levels of stress and inflammation can also make it more difficult to lose and maintain weight loss. Furthermore, increases in antioxidant status are associated with healthy body weights. Pomegranate juice and extracts attenuate stressors and inflammation and increase antioxidant status. The pomegranate extract in the present weight loss control formulations contribute to the management of both stress and inflammation in support of weight management and body weight maintenance.

Secondly, it is well established that insulin insensitivity and subsequent lack of glucose control and increased glucose fluctuations are directly related to food cravings. Pomegranate modulates glucose secretion and increase insulin sensitivity. Thus, pomegranate contributes to a reduction in food cravings in overweight and obese persons.

Further, energy levels and attitude towards physical activity directly influence adherence to any weight management program. Consumption of pomegranate extract not only improves the response to exercise training, but also reduces soreness and recovery rates following exercise. By enhancing the response to and recovery from physical activity, the pomegranate delivered in the present weight loss control formulations supports increased physical activity, making it easier to participate in physical activity on a daily basis. By reducing soreness, physical activity is a more positive experience for subjects. Pomegranate extract provides flavor and color to the present formulations and also adds benefits to help suppress appetite and influence gene expression.

Certain embodiments of the present weight management systems, programs, or methods can include a dietary component in addition to the above-recited supplement regimen. In one embodiment, important nutrients are consumed in a volume and amount that is appropriate for an individual's body size. One mechanism of measuring an appropriate amount for a body is based on the subject's (i.e. individual's) hand size. As such, in one embodiment, a serving size of a given food or nutrient can be approximately or about the size of the subject's hand.

In addition to portion size, overall intake volume is impacted by the frequency or number of servings consumed in a day. Yet further, overall nutrition is impacted by the type of nutrients or foods consumed. In one embodiment, a dietary plan or regimen that is part of a weight management system, program, or method may include from 3 to 8 servings (i.e. portions) of protein per day, from 1 to 4 servings of vegetables, from 1 to 4 servings of fruit, and from 1 to 4 servings of complex carbohydrates. In another embodiment, such a regimen may include 6 servings of protein, and 2 servings of vegetables, fruit, and complex carbohydrates per day (i.e. a 6-2-2-2 plan). Again, the portion or serving sizes are based on (i.e. roughly equivalent or equivalent to) a subject or individual's hand size. Hence, appropriate serving size for the specific individual's body is provided.

In some embodiments, the dietary plan or regimen may stipulate specific timing of consumption for the above-recited foods or nutrients. In one aspect, protein intake or consumption timing is specified. Protein is a macronutrient that plays several important roles in the body including providing amino acid building blocks for enzymes, protein structures (muscle, bone and other tissues), signaling molecules and other nitrogen requiring functions. Protein is also required for muscle cell signaling (e.g. leucine), satiety, thermogenesis, blood glucose control, maintenance of bone integrity, cardiovascular health, and calcium absorption, in addition to maintenance of lean muscle.

Dietary protein has several anti-obesigenic properties. It influences the greatest amount of satiety per calorie compared to other macronutrients (fats and carbohydrates), influences several appetite hormones, increases utilization of adipose tissue and maintains muscle mass during energy restriction, increases diet induced thermogenesis, and improves insulin resistance.

Historically, protein intake recommendations have been based on percentages of macronutrients from the diet, typically, 20-30% of calories from protein. Nutritionists now agree that this is a flawed approach. The most recent nutritional science confirms that protein intakes should be based on absolute protein levels, grams protein/kilogram body weight of the individual. This point is especially important when considering reductions in caloric intake such as when a person is dieting. For example, an individual that typically consumes 1500 kcals/day, 20% kcals from protein would consume 75 g of protein/day, but if they went down to 1,000 kcals/day, 20% kcals from protein would provide only 50 g of protein/day. Fifty grams of protein/day is not even enough protein to replace normal nitrogen losses, let alone optimally support thermogenesis, satiety, cell signaling, and calcium absorption, bone matrix remodeling and glycemic control. By basing intakes on absolute protein, rather than percentage of calories from the diet, the 6-2-2-2 dietary or eating plan maintains protein intakes even as calories are reduced, ensuring that adequate protein is available to support all protein-related metabolic processes. In other words, as a person restricts energy (kcals) on the 6-2-2-2 eating plan, they reduce energy from fat and carbohydrate, maintaining protein intakes to support essential protein metabolic functions.

The most recent recommendations for optimal protein intake are based on absolute protein intakes. For adults ≥1.6 g/kg body weight/day up to 2.5 g/kg body weight/day is considered optimal and the Institute of Medicine (TOM) has concluded that there is no Upper Limit Risk for protein intake.

Based on the latest recommendations, the protein intake for a 60 kg individual, 1.6 g/kg body weight/day would deliver 96 g/day. The 6-2-2-2 eating plan provides dietary protein proportional to body size, 6 fist-sized portions of protein/per day delivering ~15 g protein/fist size portion. A larger individual with a larger hand size will therefore consume more protein than a smaller person with a smaller hand size ensuring that each individual will consume the optimal amount of protein proportional to his/her size. In one embodiment the dietary or eating plan accommodates for 2 protein portions be consumed at each meal.

In the past, concerns have been raised that a high protein diet increases bone loss, but modern research has debunked this theory. In fact, bone volume is composed of ~50% protein and protein is essential for bone health throughout the lifespan. Previously issues were raised that protein increased urinary calcium excretion and that therefore protein increased bone loss. Recent studies have consistently reported that a high protein diet actually increases absorption of dietary calcium at a much higher rate than urinary calcium losses such that high protein intakes are associated with a net increase in calcium in bone. Furthermore, studies have demonstrated that high protein diets increase bone mineral content and reduce the risk of fractures and high protein diets combined with increased calcium, increased bone mass even further. A year-long study comparing a higher protein diet similar to the 6-2-2-2 eating plan versus a traditional low fat-high carbohydrate diet reported that the higher protein group maintained bone mineral density after one year in contrast to the low protein diet group that actually lost bone mineral density. This study highlights the issue that weight loss leads to a loss of both bone and lean muscle, and that this loss may be attenuated by the higher protein 6-2-2-2 eating plan.

Concerns have also been raised about the safety of high protein diets for diabetics, but again, recent research concludes that protein is essential for glycemic control and is actually protective in diabetics. Higher protein intakes have been demonstrated to improve glycemic control, attenuate hyperinsulinemia and are associated with reduced levels of glycosylated hemoglobin (HbAlc), a key marker of long-term blood glucose control in diabetics. These learnings indicate that not only is a high protein diet safe for diabetics, but is actually beneficial.

Lean muscle is the most metabolically active tissue in the body, playing a key role in thermogenesis, energy balance and weight management. Unfortunately, loss of lean muscle is a typical side effect of any weight loss program. The loss of metabolically active lean muscle during weight loss makes it very difficult for an individual to maintain their weight loss over time. Consequently, dieters that lose muscle mass during a weight loss program are more likely to regain the lost weight than those that maintain their lean muscle during weight loss. Higher protein diets, such as the 6-2-2-2 plan, attenuate the loss of lean muscle during weight loss, maintaining this metabolically active lean tissue and supporting weight maintenance following the 90 days of the plan.

Figure 1:
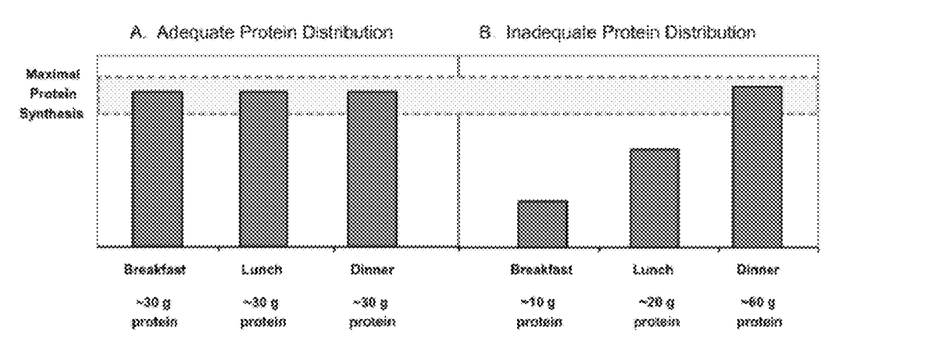
FIG. 1 is a graphical representation of ingestion of 90 g of protein, distributed evenly over 3 meals (A) as compared to typical ingestion of 90 g of proteins unevenly distributed throughout the day (B). Stimulating muscle protein synthesis to a maximal extent during the meals shown in (A) is more likely to provide a greater 24 h protein anabolic response than an unequal protein distribution.

In addition to sparing lean muscle and preventing bone loss during a weight management program, the dietary protein delivered in the present dietary or nutrition regimens of the present invention, such as the 6-2-2-2 eating plan, also provide optimal levels of the essential branched chain amino acid leucine. Leucine acts as a signaling molecule stimulating the synthesis of new muscle following a protein-containing meal. Leucine promotes muscle synthesis by signaling changes in gene expression. In order to stimulate protein synthesis, a minimum amount of leucine (2.5-3 g/meal) is required. On average, 30 grams of protein in a single meal delivers enough leucine to stimulate muscle synthesis. In order to address this issue, the 6-2-2-2 eating plan distributes protein intake evenly throughout the day. Most people eat the majority of their protein during their evening meal which means they consume predominately carbohydrates in morning and afternoon meals, signaling the body to store fat, not burn it and only build protein after the evening meal. Interestingly, most people consume 70-90% of protein in the evening meal. It is proposed that by distributing the dietary protein to achieve between about 10 g to 30 g of protein per meal, lean tissue is stimulated and the body will draw upon adipose tissues to meet energy demands, thus impacting overall weight. (FIG. 1)

As a result, in one aspect, a dietary component of the present weight management or maintenance systems, programs, or methods may include a plan where a substantial amount of protein is consumed at each meal. In one aspect, the amount may be at least about 10 grams. In another aspect, the amount may be at least about 20 grams. In a further aspect, the amount may be at least about 30 grams. In a further aspect, the amount may be from about 10 grams to about 50 grams.

It should be emphasized that the dietary component of the present weight management systems, programs, or methods are very different from other known weight loss plans as the present plans focus on maintaining optimal levels of protein and distributes that protein evenly throughout the day. The exemplary 6-2-2-2 program or plan delivers moderate amounts of protein in contrast to very high protein diets such as "Atkins" and "Paleo Diet". Since the exemplary 6-2-2-2 eating plan is balanced and because it is designed to deliver optimal protein levels, as well as fruit and vegetable intakes, it can therefore be continued long after other portions of the present weight management systems, programs, and methods are completed, or example, the 90 day plan described herein. By helping individuals to achieve a healthy eating lifestyle, the exemplary 6-2-2-2 eating plan can be maintained throughout one's life.

The one form in which protein may be consumed under the present dietary regimens or plans is using protein containing shakes. Such shakes can make it easy to incorporate a minimum of 30 grams of protein per meal. Exemplary shakes can contain at least about 12-15 grams of highly biologically available protein (for example whey protein) and a good source of an essential amino acid, leucine. Whey protein offers a number of benefits as well as influences metabolic rate and thermogenesis. Whey protein ingestion along with energy reduction has shown to increase utilization of adipose tissue (burn fat) and maintenance of lean body mass as compared to energy reduction alone. Furthermore whey protein has been shown to be superior (i.e. soy) to other sources of protein in utilization of adipose tissue, increase weight loss and preserve lean body mass.

In one embodiment, a shake can be formulated to include tart cherry powder that has been identified as a food ingredient that shifts gene expression in muscle and adipose tissue in a positive direction and supports healthy weight loss as previously mentioned.

EXAMPLES

A study was undertaken to understand the effects of natural compounds as supplements to assist along with an eating plan to influence body composition changes and safety through laboratory values in subjects participating in a 3 month study. The study was descriptive in nature and to understand the expected results of males and females participating in the study.

Given the promising results, the excellent safety profile, and the complementary mechanisms of action Fucoxanthin, *Citrus* bioflavonoids, Onion extract, *Capsicum*, Dark chocolate extract, and Tart cherry powder, it was hypothesized that a proprietary blend of these ingredients may improve the overall weight loss along with a healthy dietary program.

Potential subjects who met the inclusion and exclusion criteria were screened and enrolled into the study. Seventy three healthy subjects were recruited to participate in this study. There were 5 female subject that decided to withdraw their consent, one female was withdrawn because of non-compliance with product consumption, one male subject was a screen failure, and one male subject was lost to follow-up which left a total of 65 evaluable subjects (females n=44 and males n=211 whose ages ranged from 25 to 65 years and body mass indexes (BMI) ranged from 25-40 kg/m².

The study inclusion criteria were as follows:
1. Females and Males aged 25-65 years
2. Signed informed consent
3. BMI between 25 and 40 kg/m2
4. A resting normotensive blood pressure is defined as a systolic blood pressure between 90-145 mmHg and a diastolic blood pressure of 50 90 mmHg
5. Use of effective method of contraception by females of childbearing [potential and agreement to continue to practice an acceptable method of contraception for the duration of their participation in the study]. Acceptable methods of contraception include oral, injectable, or implantable contraceptives; intrauterine devices, diaphragm plus spermicide; abstinence (must agree to use double-barrier method if they become sexually active}, transdermal patch, or any double barrier method including a vasectomized sexual partner. Women who have had a hysterectomy or tubal ligation at least 6 months prior to Visit for who have been post-menopausal for at least 1 year prior to Visit 1 are not considered to be of child-bearing potential.
6. Ability to speak and understand English
7. Willing to fast the morning of visit where blood samples are taken Exclusion Criteria
1. Self-reported chronic condition that may affect subject safety (e.g., diabetes, cardiovascular disease) or significantly impact product effectiveness (e.g., chronic fatigue)
2. Pregnancy/suspected pregnancy, breastfeeding or planning to become pregnant during the course of the study.
3. Use of Antihypertensive medication for less than 4 months or unregulated clinically blood pressure.
4. Having undergone gastroplasty or bariatric surgery in the past 10 years.
5. Taking medication (e.g., thyroid medication), must be stable for at least four months.
6. Allergies to any ingredients contained in the Nutritional Supplement.
7. Medical treatment for insomnia or depression within 30-days prior to the screening visit.
8. Tobacco (e.g. cigarettes, chewing tobacco, pipe, nicotine patches) use within 30-days prior to the screening visit.
9. Planned surgical procedure during the course of the study.
10. Currently participating in another study or have done so within 30 days prior to the screening visit or is likely to enroll in another clinical or nutritional study.
11. Currently taking any medication or supplement for the use of weight loss must be discontinued prior to Visit 1Baseline Day 0.
12. Currently participating in a weight loss program or participated in a weight loss program in the past 6 months.

The study was conducted with good clinical practices and standards. Measurements were made at Baseline, 14 days, 30 days, 60 days, 90 days (see schedule of events) as well as with accredited laboratories.

Schedule of Events

This study was an Open-label, Single-Center Study on the Effects of a Nutritional Supplement Combination on Body Weight Management over a 90-day period in Men and Women ages 25 to 65.

| Clinical Visit Number Procedures | V1 Day 0 Screening/ Baseline | V2 Day 15 ± 3 Days | V3 Day 30 ± 3 Days | V4 Day 60 ± 3 Days | V5 Day 90 ± 3 Days | V6 Day 97 ± 3 Days |
|---|---|---|---|---|---|---|
| Inclusion/Exclusion criteria review - Inform subjects of bonus possibility and they may be asked to share their experience at the end of the study | X | | | | | |
| Subject Informed Consent | X | $x^1$ | $x^1$ | $x^1$ | $x^1$ | |
| Medical History review of systems | X | | | | | |
| Prior and concomitant medication history | X | X | X | X | X | |
| Height | X | | | | | |
| Weight & BMI | X | X | X | X | X | |
| Body measurements (waist, hip, arm, ankle) | X | X | X | X | X | |
| Vital signs (BP, pulse, resps, & temps) | $X^3$ | $X^3$ | $X^3$ | $X^3$ | $X^3$ | |
| Abbreviated Physical Exam | X | | | | X | |
| Photos (shorts/sports bra or full swim suit) | X | X | X | X | X | |
| Fasting Safety Labs (chemistry, hematology, Coagulation) | X | X | | | X | |
| BioPhotonic Scanner | X | X | X | X | X | |
| Bod Pod: Body Fat Analyzer Test | X | X | X | X | X | |
| Resting Metabolic Rate Test (RMR) | X | X | X | X | X | |
| Gene Expression Panel whole blood and Lipid Panel | X | X | | | X | |
| Pregnancy test | $x^2$ | | | | | |
| DPWA Pulse Wave Analyzer | X | | | | X | |
| Nutritional Supplement Dispensing | X | | X | X | | |
| Unused Nutritional Supplement Collection | | X | X | X | X | |
| Nutritional Supplement Accountability | | $X^4$ | $X^4$ | $X^4$ | $X^4$ | |
| Monitor of Adverse Events | | X | X | X | X | |
| Questionnaire IWQOL Hunger/Appetite + questionaire | X | X | | | X | |
| Diet Menu - 6-2-2-2-2 Approx 1,200 calories/day M/F | X | X | X | X | X | X |
| Calibrate the Pedometer | X | | | | | |
| Daily Diary | X | X | X | X | X | |

[1]For Amended ICF's
[2]Urine at Visil 1
[3]Vital signs collected after the subject has been sitting for a minimum of 5 minutes and collected using subjects dominant arm Efficacy Assessment Weight and body compositional changes were determined by BodPod, resting metabolic rate (CPET/Quark), body measurements (Waist, Hip, Arm, and Ankle Circumference), and questionnaires to determine quality of life and hunger changes.

Safety Assessment

Safety was assessed by changes in blood chemistries/hematology, and description and tabulation of all adverse events (AE's), nutritional supplement emergent AEs (TE-AE's), classified by severity grade, relatedness to the Nutritional Supplement, and organ class according to the investigator's judgment.

Serious adverse events (SAE's) were followed by the investigator until they had resolved, reached a stable condition, or the subject was lost to follow-up. Vital signs (heart rate, blood pressure, respiratory rate, and oral temperature) were collected at Visits 1 through 5 using the subject's dominant arm.

Descriptive Analysis

The results from this study were meant to be descriptive in nature so as to have an understanding what individuals can expect when using the system (both from a safety and efficacy standpoint). A comparative group was also included regarding the gene expression results (in a subset of subjects completing the 90 day weight management system). In this work a group of subjects was used from another clinical study in which gene expression work was performed in the identical manner but the subjects were in a BMI range of 22-26. This comparison helped in examining baseline blood values and differences in pathways between normal and overweight/obese. Then following the 90 days of being on the program, changes in their gene expression from baseline and the direction or similarities to a group of subjects that were not overweight or obese could be compared.

Participants and Body Composition

There were 73 subjects that were screened to participate in the study. Seventy two subjects were randomized to participate. There were 69 subjects (Females n=47; Males n=22) that completed day 14 and 66 (Females n=45; Males n=21) that completed 90 days of the study (see Table 4). The average age of the subjects were 43.8 years of age with an average baseline BMI of 31.1.

The products were well tolerated and the compliance of consuming the products were 96% overall with 96% and 94% for women and men, respectively.

TABLE 4

Number of subjects, average age, and body mass index (BMI)

| | Subjects (n) Enrolled and completed 14 days | Subjects (n) Completed 90 days | Age (years)* | Baseline BMI* |
|---|---|---|---|---|
| Females | 47 | 45* | 44.1 ± 1.4 | 31.1 ± 0.5 |
| Males | 22 | 21* | 43.21 ± 1.3 | 31.2 ± 0.8 |
| Total | 69 | 66 | 43.8 ± 1.2 | 31.1 ± 0.5 |

The reasons for subjects dropping from the study were:
1. Voluntarily withdrew n = 6
2. Non-compliance (not consuming the products) n = 1
*means ± SEM There was a dramatic loss of body fat (day 90) and a maintenance of fat free-mass (see Table 5).

TABLE 5

Changes in body fat, % body fat, fat-free mass, and body weight (Means ± SEM).

| | Change in Body Fat (lbs) Day 1-90 | Change in Body Fat (lbs) Day 0-14 | Change in Body Fat Day 0-90 | Change in Fat Free Mass (lbs) Day 0-14 | Change in Fat Free Mass (lbs) Day 0-90 | Change in Body Weight (lbs) Day 0-14 | Change in Body Weight (lbs) Day 0-90 |
|---|---|---|---|---|---|---|---|
| Females | −12.9 ± 1.9 | −1.3% | −6.0% | +0.6 ± 0.7 | +6.6 ± 1.0 | −3.4 ± 0.4 | −6.4 ± 1.3 |
| Males | −19.7 ± 2.0 | −1.6% | −8.5% | −0.5 ± 0.8 | +7.5 ± 0.9 | −5.4 ± 0.7 | −12.1 ± 2.2 |
| Total | −15.1 ± 1.2 | −1.4% | −6.8% | +0.2 ± 0.5 | +7.0 ± 0.7 | −3.8 ± 0.4 | −8.2 ± 1.2 |

Along with the changes in body composition there was a decline in BMI and an increase in basal metabolic rate as measured in a subset of subjects (see Table 6). There was some difficulty on the part of the study staff in obtaining accurate metabolic rates and for subjects that had values that were not physiologically possible their RMR values were removed from the analysis. Respiratory quotient (RQ=$CO_2$ eliminated/$O_2$ retained) a measure of substrate (carbohydrate vs fat) utilization only changed modestly.

TABLE 6

Changes in BMI, resting metabolic rates, and R-values (means ± SEM).

| | Change in BMI Day 0-14 | Change in BMI Day 0-90 | Change in Resting Metabolic Rate (Kcals) Day 0-14* | Change in Resting Metabolic Rate (Kcals) Day 0-90* | Respiratory Quotient (change) Day 0-90* |
|---|---|---|---|---|---|
| Females | −0.5 ± 0.1 | −1.1 ± 0.2 | −33.7 ± 33.6 | +150.3 ± 35.7 | 0.85 (0.13 ± 0.01) |
| Males | −0.8 ± 0.1 | −1.8 ± 0.3 | +13.8 ± 51.5 | +116.6 ± 75.5 | 0.85 (−0.03 ± 0.02) |
| Total | −0.6 ± 0.1 | −1.3 ± 0.2 | −15.9 ± 28.2 | +147.1 ± 34.4 | 0.85 (−0.01 ± 0.01) |

*A subset of subjects were included because there were several subjects that had RMR below 1,000 kcals at baseline. Therefore any subject with a RMR below 1,000 was excluded, total n = 50, females n = 33, males n = 17.

Body Measurements

Noticeable changes in body measurements and circumferences (waist, hip, arm and ankle) were noted (see Table 7). There were measurable changes that occurred by day 14.

TABLE 7

Changes in body measurements (means ± SEM).

| | Change in Waist Circumference (cm) Day 0-14 | Change in Waist Circumference (cm) Day 0-90 | Change in Waist Circumference (cm) Day 0-14 | Change in Hip Circumference (cm) Day 0-90 | Change in Arm Circumference (cm) Day 0-14 | Change in Arm Circumference (cm) Day 0-90 | Change in Ankle Circumference (cm) Day 0-14 | Change in Ankle Circumference (cm) Day 0-90 |
|---|---|---|---|---|---|---|---|---|
| Females | -2.2 ± 0.5 | -7.4 ± 0.9 | -1.9 ± 0.4 | -6.4 ± 0.7 | -0.9 ± 0.3 | -2.3 ± 0.3 | -0.7 ± 0.1 | -1.6 ± 0.2 |
| Males | -1.8 ± 0.8 | -7.9 ± 1.2 | -0.9 ± 0.5 | -5.8 ± 1.2 | -0.5 ± 0.3 | -1.9 ± 0.3 | -0.6 ± 0.2 | -1.0 ± .03 |
| Total | -2.1 ± 0.4 | -7.4 ± 0.7 | -1.5 ± 0.3 | -6.1 ± 0.6 | -0.8 ± 0.2 | -2.2 ± 0.3 | -0.7 ± 0.1 | -1.4 ± 0.3 |

Labs and Safety

In determining safety, blood chemistries and complete counts were measured at baseline and at day 90 (see Table 8). These values were all within the normal range except for LDL cholesterol and ALT. The LDL did not change from baseline and the study physician noted that the higher levels of LDL were not clinically significant. Regarding the ALT, there was one female subject that had elevated ALT at Day 90 which caused the average to be slightly above the normal range. The study physician noted that this level of ALT was not clinically significant. If this subject is not included in the averages, the ALT level was 35.6 U/L.

TABLE 8

Blood chemistries and complete blood cell count of subjects at baseline and day 90 (means ± SEM).

| | Total Baseline | Total 90 Day | Females Baseline | Females 90 Day | Males Baseline | Males 90 Day | Reference Ranges |
|---|---|---|---|---|---|---|---|
| Sodium (mmol/L) | 138.4 ± 0.2 | 138.8 ± 0.2 | 138.6 ± 0.2 | 138.6 ± 0.3 | 138.0 ± 0.2 | 139.3 ± 0.4 | 136-140 |
| Potassium (mmol/L) | 4.0 ± 0.04 | 4.2 ± 0.04 | 4.0 ± 0.05 | 4.1 ± 0.05 | 4.2 ± 0.1 | 4.2 ± 0.1 | 3.5-5.1 |
| Chloride (mmol/L) | 105.0 ± 0.3 | 104.2 ± 0.2 | 105.5 ± 0.3 | 104.4 ± 0.2 | 104.1 ± 0.7 | 103.8 ± 0.4 | 3.5-5.1 |
| Urea Nitrogen (BUN/Urea) | 13.4 ± 0.5 | 14.0 ± 0.5 | 12.6 ± 0.6 | 13.4 ± 0.6 | 15.3 ± 0.8 | 15.7 ± 0.8 | 8-26 |
| Glucose (mg/dL) | 87.4 ± 1.2 | 88.6 ± 1.1 | 85.9 ± 1.5 | 87.6 ± 1.3 | 90.7 ± 1.3 | 90.7 ± 1.9 | 96-109 |
| Hematocrit (%) | 43.2 ± 0.3 | 42.9 ± 0.5 | 42.5 ± 0.6 | 41.3 ± 0.6 | 48.8 ± 0.9 | 45.7 ± 0.7 | Females 34.7-50.0 Males 36-50 |
| Hemoglobin (g/dL) | 14.8 ± 0.2 | 14.4 ± 0.2 | 14.4 ± 0.2 | 13.8 ± 0.2 | 15.7 ± 0.3 | 15.5 ± 0.1 | Females 12.1-17.1 Males 12-18 |
| Prothrombin time (Seconds) | 10.8 ± 0.1 | 11.0 ± 0.1 | 10.6 ± 0.1 | 10.9 ± 0.1 | 11.2 ± 0.2 | 11.1 ± 0.1 | 9.7-13.3 |
| Aspartate aminotransferase AST (U/L) | 22.0 ± 1.0 | 29.2 ± 7.8 | 21.7 ± 1.2 | 32.5* ± 11.6 | 23.4 ± 1.1 | 22.7 ± 1.1 | 15-37 |
| Alanine transaminase ALT (U/L) | 24.6 ± 1.7 | 58.4 ± 20.4 | 22.8 ± 2.0 | 65.8* ± 30.2 | 27.9 ± 2.9 | 42.6 ± 1.7 | 30-65 |
| Cholesterol (mh/dL) | 183.7 ± 3.9 | 187.4 ± 4.5 | 185.8 ± 3.9 | 185.8 ± 5.1 | 179.6 ± 9.0 | 190.8 ± 9.3 | <200 |
| LDL (mg/dL) | 111.1 ± 3.3 | 118.4 ± 3.6 | 11.7 ± 3.2 | 115.8 ± 4.0 | 108.9 ± 8.1 | 122.4 ± 7.5 | <100 |
| HDL (mg/dL) | 50.4 ± 1.5 | 50.2 ± 1.3 | 45.3 ± 2.2 | 52.2 ± 1.7 | 45.0 ± 1.7 | 48.0 ± 1.2 | 38-50 |
| Cholesterol/HDL | 3.8 ± 0.1 | 3.9 ± 0.1 | 3.7 ± 0.1 | 3.7 ± 0.1 | 4.0 ± 0.2 | 4.1 ± 0.2 | |
| Triglycerides (mg/dL) | 114.2 ± 6.6 | 88.8 ± 5.4 | 107.2 ± 7.1 | 84.0 ± 6.6 | 133.8 ± 13.9 | 100.9 ± 9.2 | <150 |
| White Blood Cell Count (1000/mm3) | 635 ± 0.2 | 6.2 ± 0.2 | 6.7 ± 0.3 | 6.3 ± 0.3 | 6.3 ± 0.3 | 6.0 ± 0.3 | 4.5-11 |
| Red Blood Cell Count (million/mcl) | 4.8 ± 0.1 | 4.7 ± 0.1 | 4.6 ± 0.0 | 4.6 ± 0.1 | 5.1 ± 0.1 | 5.1 ± 0.1 | 4.3-5.8 |
| Mean corpuscular volume - MCV (fl) | 90.3 ± 0.8 | 87.9 ± 0.4 | 90.4 ± 1.1 | 87.4 ± 2.0 | 90.1 ± 0.8 | 85.6 ± 0.9 | 84-100 |
| Mean corpuscular hemoglobin - MCH (pg) | 30.2 ± 0.3 | 29.9 ± 0.3 | 30.1 ± 0.3 | 29.9 ± 0.5 | 30.3 ± 0.3 | 30.0 ± 0.4 | 27.5-33.5 |
| Mean corpuscular hemoglobin concentration - MCHC (gm/dL) | 33.4 ± 0.3 | 33.6 ± 0.1 | 33.3 ± 0.2 | 33.5 ± 0.1 | 33.7 ± 0.2 | 33.7 ± 0.2 | 31-37 |
| Mean platelet volume - MPV (fl) | 8.8 ± 0.1 | 9.2 ± 0.1 | 8.9 ± 0.1 | 9.3 ± 0.1 | 8.5 ± 0.9 | 8.8 ± 0.2 | 7.4-10.4 |
| Red blood cell distribution width - RDW(%) | 1.1 ± 0.2 | 13.8 ± 0.2 | 14.3 ± 0.2 | 14.0 ± 0.3 | 13.8 ± 0.3 | 13.5 ± 0.2 | 11.6-15.5 |
| Platelet count - PLT (1000/cm3) | 258.6 ± 4.4 | 248.0 ± 6.7 | 266.5 ± 7.2 | 252.1 ± 7.5 | 244.5 ± 12.1 | 243.2 ± 13.8 | 140-440 |
| Segs (%) | 62.0 ± 1.0 | 59.9 ± 2.2 | 62.9 ± 1.0 | 59.8 ± 2.0 | 60.4 ± 2.4 | 59.5 ± 5.7 | 44.0-80.0 |
| Lymphocytes (%) | 29.0 ± 0.3 | 30.2 ± 1.3 | 28.4 ± 0.9 | 30.6 ± 1.4 | 30.1 ± 1.1 | 29.9 ± 2.9 | 10.0-42.8 |
| Monocytes (%) | 6.9 ± 0.2 | 6.6 ± 0.3 | 6.3 ± 0.2 | 6.5 ± 0.3 | 7.9 ± 0.3 | 6.9 ± 0.8 | 2.7-13.0 |

TABLE 8-continued

Blood chemistries and complete blood cell count of subjects at baseline and day 90 (means ± SEM).

|  | Total | | Females | | Males | | |
| --- | --- | --- | --- | --- | --- | --- | --- |
|  | Baseline | 90 Day | Baseline | 90 Day | Baseline | 90 Day | Reference Ranges |
| Eosinophils (%) | 2.2 ± 0.2 | 2.2 ± 0.2 | 1.8 ± 0.1 | 2.0 ± 0.2 | 2.9 ± 0.5 | 2.7 ± 0.5 | 0.0-8.1 |
| Basophils (%) | 0.6 ± 0.0 | 1.0 ± 0.1 | 0.5 ± 0.1 | 1.1 ± 0.2 | 0.6 ± 0.0 | 1.0 ± 0.2 | 0.0-1.4 |

*One female subject had AST of 528 U/L and ALT of 362 U/L at day 90. Physician indicated that these were not clinically significant. The other enzymes in each group were within the normal ranges.

There was little difference between baseline and day 90 for systolic and diastolic blood pressures, pulse rate, respirations, and body temperature (see Table 9).

TABLE 9

Vital Signs (average ± SEM)

|  | Total | | Females | | Males | |
| --- | --- | --- | --- | --- | --- | --- |
|  | Baseline | 90 Day | Baseline | 90 Day | Baseline | 90 Day |
| Systolic Blood Pressure (mmHG) | 125.7 ± 1.2 | 123.2 ± 1.3 | 123.2 ± 1.6 | 121.1 ± 1.3 | 128.8 ± 1.7 | 127.7 ± 2.6 |
| Diastolic Blood Pressure (mmHg) | 79.2 ± 0.7 | 77.8 ± 0.9 | 78.8 ± 0.8 | 78.2 ± 1.0 | 79.7 ± 1.4 | 77.6 ± 1.7 |
| Pulse rate (beats/min) | 69.9 ± 1.5 | 68.7 ± 1.2 | 71.6 ± 1.7 | 69.9 ± 1.3 | 66.6 ± 2.7 | 66.0 ± 2.5 |
| Respiration (breaths/minute) | 14.9 ± 0.2 | 15.5 ± 0.2 | 14.9 ± 0.3 | 15.5 ± 0.2 | 15.0 ± 0.3 | 15.5 ± 0.2 |
| Body temperature (° F.) | 97.2 ± 0.1 | 97.0 ± 0.1 | 97.3 ± 0.1 | 97.0 ± 0.1 | 97.1 ± 0.1 | 97.0 ± 0.2 |

There was an increase in biophotonic scanner score and by using digital pulse wave analyzer the estimated biological age was lower than chronological age at baseline and dropped slightly, particularly for the females at day 90 (see Table 10).

TABLE 10

Biophotonic Scanner Scores at baseline and day 90 (means ± SEM) along with the chronological ages and estimated biological ages.

|  | Biophotonic Scanner Score (Raman Units) Baseline | Biophotonic Scanner Score (Raman Units) Day 90 | Chronological Age of Subjects at baseline (Years) | *Estimated Biological Age at Baseline (Years) | Estimated Biological Age at day 90 (Years) |
| --- | --- | --- | --- | --- | --- |
| Females | 24,694 ± 1,284 | 29,987 ± 1,480 | 44.1 + 1.4 | 36.9 ± 1.6 | 36.5 + 1.7 |
| Males | 27,380 ± 1,940 | 29,943 ± 2,080 | 43.2 + 1.3 | 34.4 ± 1.9 | 34.8 ± 1.0 |
| Total | 25,351 ± 1,070 | 29,936 ± 1,198 | 43.8 + 1.2 | 36.0 ± 1.3 | 35.4 ± 1.0 |

*Based on vascular stiffness

There were no Serious Adverse Events Reports. There was a total of 10 adverse events report by 6 subjects. Table 11 lists all the related adverse events as probably or possibly related to the products.

TABLE 11

Listing of adverse events probably or possibly related to the products (total of 6 subjects reported adverse events, 6/73-8.2% of subjects).

|  | Number of Episodes |
| --- | --- |
| Gastrointestinal Related |  |
| Upset stomach | 2 |
| Nausea | 2 |

TABLE 11-continued

Listing of adverse events probably or possibly related to the products (total of 6 subjects reported adverse events, 6/73-8.2% of subjects).

|  | Number of Episodes |
| --- | --- |
| Vomiting | 1 |
| Constipation | 1 |
| Diarrhea | 1 |
| Abdominal cramps | 1 |
| Other |  |
| Headache | 1 |
| Insomnia | 1 |

Questionnaires

Subjects were given questionnaires regarding overall satisfaction with the program, if they had tried other weight loss programs they were asked to respond how the tested system compared. They were also asked whether they could notice a change in their silhouette at 2 weeks and at day 90.

Furthermore, they were asked if they noticed their clothing fitting differently or if the program was helping them lose weight. Lastly, a questionnaire regarding the subjects' quality of life was administered but the data is still being evaluated and will be included at a later date.

Self-Reported Questionnaires: After 2 Weeks on Program
1) 83% of subjects had an overall positive satisfaction with the program
2) 96% of Subjects said this program is better or extremely better than other programs they have tried (81% of participants had been on other programs).

In addition, 85% of subjects notice a change in body silhouette, 98% indicated that their clothes fit differently, and 91% indicated that the program was helping them to lose weight.

Report after 12 Weeks of Program Participation
1) 73% of subjects had an overall positive satisfaction with the program
2) 87% of Subjects said this program is better or extremely better than other programs they have tried (81% of participants had been on other programs).

In addition, 92% of subjects notice a change in body silhouette, 94% indicated that their clothes fit differently, and 89% indicated that the program was helping them to lose weight.

Discussion

Eighty percent of participants lost weight (Females, n=32 and Males, n=21) while a few subjects maintained or gained weight (Females, n=13 and Males, n=O). Interestingly, there was a dramatic loss of body fat (approximately 20 pounds and 13 pounds for females and males, respectively) and maintenance of fat-free body mass (approximately 7 pounds). These effects were seen both in the females and males. The study found similar results to another study which noted a loss of fat and maintenance of fat-free mass by providing approximately 1.6 g protein/kg body weight. These effects are attributed to the system, since there were no controls for diet or supplements alone. The study findings support the program of losing primarily fat and maintaining loss of fat-free mass during restricting energy.

It is important to recognize that weight management is not simply about reduction in body weight. It is advantageous to maintain lean tissue (muscle), in that it lean tissue has a higher metabolic rate.

Many weight loss programs note 20-40% of the weight as fat-free mass lost simply because the body meets its energy demands from muscle or fat. Particularly when carbohydrates are consumed it signals the body, via insulin, to shift from releasing to storing free fatty acids. This leads to energy demands being met by protein. The strategy in this study was to provide adequate amount of protein (2 portions of protein providing at least 30 grams of protein) at each meal to signal the body to maintain muscle and meet energy demands via fat. The finding that the majority of weight being lost was primarily fat is an important finding. This finding that body composition changes are occurring is supported by the changes in body measurements (i.e. waist, hip, arm, calf, and ankle circumference).

This was also supported by the response of the subjects to the questionnaire that they were noting changes in their silhouette as well their clothing fitting differently. Furthermore, the subjects noted or observed changes within the first 14 days of the program.

The products and program were well accepted and there was a low dropout rate from the study as well as very few adverse events noted. It was anticipated that the ingredients selected were safe and this study confirms very little change in labs (metabolic and lipid profiles) and complete blood cell count as well as vital signs did not change; indicating that the products and program are safe.

Based on self-reported questionnaires, the subjects indicated that the program assisted in weight loss and a majority of subjects that had used weight loss programs or products indicated that this program was better than other programs.

The Biophotonic Scanner scores increased slightly over the course of the study. This appears to be the change in dietary habits and increased consumption of carotenoid containing foods (fruits and vegetables) in that the subjects could not consume dietary supplements which can also be a source of carotenoids.

It was interesting that the resting metabolic rate increased but the RQ values did not change much. An RQ value of 1.00 would indicate the utilization of carbohydrates while an RQ value of 0.7 would indicate the utilization of fat to meet energy demands. There is complexity in determining RQ of utilizing proteins or amino acids but since the fat-free mass did not change (actually increased slightly over the course of the study) no conclusion can be made regarding the RQ values and maintenance of lean tissue. Overall, the subject were utilizing a mixture of carbohydrates and fats (RQ of 0.85) to meet their energy demands. This may have also indicated that the subjects were in a fasted state and made it difficult to see any shifts in the respiratory quotient, even though the subjects appear to be utilizing primarily fat.

By using the digital pulse wave analyzer, it was possible to measure the arterial wall elasticity or stiffness and estimate the biological arterial age. There was a slight overall improvement, which was primarily from improvement in the females with weight loss. However, it is interesting that the biological age estimation was significantly lower at baseline as compared to the chronological age by approximately six years. This may indicate that the population included in the study were healthy other than being overweight or obese.

While the forgoing examples are illustrative of the specific embodiments in one or more particular applications, it will be apparent to those of ordinary skill in the art that numerous modifications in form, usage and details of implementation can be made without departing from the principles and concepts articulated herein. Accordingly, no limitation is intended except as by the claims set forth below.

What is claimed is:

1. A composition consisting essentially of:
a) a tablet or capsule which is a weight loss stimulator formulation that stimulates weight loss in a human consisting essentially of therapeutically effective amounts of red orange fruit extract, green tea leaf extract, onion bulb extract, brown seaweed extract, a *citrus* bioflavanoid, and cayenne fruit extract; or
b) a tablet or capsule which is a weight loss control formulation that aids a human in controlling his or her appetite and calorie consumption in said human consisting essentially of therapeutically effective amounts of cocoa bean extract, tart cherry fruit extract, pomegranate fruit extract, and green tea leaf extract.

2. The composition of claim 1, wherein the weight loss stimulator formulation is an oral dosage capsule.

3. The composition of claim 1, wherein the red orange fruit extract is present in amount of from about 50 mg to about 250 mg.

4. The composition of claim 3, wherein the amount of red orange fruit extract is about 83.3 mg.

5. The composition of claim 1, wherein the green tea extract is present in an amount of about 30 to about 860 mg.

6. The composition of claim 5, wherein the amount of green tea extract is either about 50 mg or about 107.5 mg.

7. The composition of claim 1, wherein the onion bulb extract is present in an amount of from about 10 mg to about 75 mg.

8. The composition of claim 7, wherein the amount of onion bulb extract is about 25 mg.

9. The composition of claim 1, wherein the cayenne fruit extract is present in an amount of from about 10 mg to about 52 mg.

10. The composition of claim 9, wherein the amount of cayenne fruit extract is about 16.7 mg.

11. The composition of claim 1, wherein the *citrus* bioflavonoids are present in an amount of from about 20 mg to about 100 mg.

12. The composition of claim 11, wherein the amount of *citrus* bioflavonoids is about 33.3 mg.

13. The composition of claim 1, wherein the weight loss control formulation is an oral dosage capsule.

14. The composition of claim 1, wherein the cocoa bean extract is present in an amount of from about 150 mg to about 1500 mg.

15. The composition of claim 14, wherein the amount of cocoa bean extract is about 187.5 mg.

16. The composition of claim 1, wherein the tart cherry extract is present in an amount of from about 75 mg to about 600 mg.

17. The composition of claim 16, wherein the amount of tart cherry extract is about 75 mg.

18. The composition of claim 1, wherein the pomegranate extract is present in an amount of from about 60 mg to about 500 mg.

19. The composition of claim 18, wherein the amount of pomegranate extract is about 62.5 mg or about 150 mg.

20. The composition of claim 1, wherein the brown seaweed extract is present in an amount of from about 50 mg to about 250 mg.

* * * * *